United States Patent
Strathmann

(10) Patent No.: US 9,962,706 B2
(45) Date of Patent: May 8, 2018

(54) SAMPLE TUBE ADAPTERS AND METHODS OF USE THEREOF

(71) Applicant: University Of Utah Research Foundation, Salt Lake City, UT (US)

(72) Inventor: Frederick G. Strathmann, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days. days.

(21) Appl. No.: 15/028,132

(22) PCT Filed: Oct. 7, 2014

(86) PCT No.: PCT/US2014/059558
§ 371 (c)(1),
(2) Date: Apr. 8, 2016

(87) PCT Pub. No.: WO2015/054305
PCT Pub. Date: Apr. 16, 2015

(65) Prior Publication Data
US 2016/0236197 A1 Aug. 18, 2016

Related U.S. Application Data

(60) Provisional application No. 61/888,993, filed on Oct. 9, 2013.

(51) Int. Cl.
*B01L 3/00* (2006.01)
*G01N 35/00* (2006.01)

(52) U.S. Cl.
CPC ........ *B01L 3/563* (2013.01); *B01L 3/50853* (2013.01); *B01L 2200/02* (2013.01);
(Continued)

(58) Field of Classification Search
CPC ...................................................... B01L 3/563
(Continued)

(56) References Cited

U.S. PATENT DOCUMENTS

| 3,422,998 A | 1/1969 | Murray |
| 4,132,225 A | 1/1979 | Whattam |

(Continued)

FOREIGN PATENT DOCUMENTS

| EP | 0273548 A2 | 7/1988 |
| WO | WO-9855232 A1 | 12/1998 |

OTHER PUBLICATIONS

International Search Report PCT/ISA/210 for International Application No. PCT/US2014/059558 dated Jan. 13, 2015.
(Continued)

*Primary Examiner* — Brian J. Sines
(74) *Attorney, Agent, or Firm* — Harness, Dickey & Pierce, PLC

(57) ABSTRACT

Sample tube adapters dimensioned to fit into one or more sample tubes in order to prevent carryover or contamination between sample tubes that are adjacent to one another during one or more stages of sample preparation. Methods for use of such sample tube adapters and methods for preventing carryover or contamination between sample tubes that are prepared adjacent to one another are also described. The apparatus described herein was developed to mitigate or eliminate cross-well contamination identified in high-throughput assays, e.g., 96-well based assays. In one embodiment, the apparatus is designed to fit onto the top of a standard 96-well plate and is kept in place during one or more stages of sample preparation, e.g., the entire forced-air drydown portion of sample preparation.

27 Claims, 9 Drawing Sheets

(52) U.S. Cl.
CPC . *B01L 2200/0678* (2013.01); *B01L 2200/141* (2013.01); *B01L 2300/048* (2013.01); *B01L 2300/0829* (2013.01); *B01L 2300/0832* (2013.01); *G01N 2035/00287* (2013.01)

(58) Field of Classification Search
USPC ....... 422/501, 502, 544, 547, 549, 553, 554; 436/43, 174, 180
See application file for complete search history.

(56) References Cited

U.S. PATENT DOCUMENTS

| | | | | |
|---|---|---|---|---|
| 4,454,962 | A * | 6/1984 | Greenspan | B65D 83/04 221/288 |
| 4,990,129 | A * | 2/1991 | Nielsen | B04B 5/0414 494/20 |
| 5,337,931 | A * | 8/1994 | Kitterman | B65D 47/247 222/525 |
| 5,378,433 | A * | 1/1995 | Duckett | B01L 9/06 206/443 |
| 5,968,620 | A | 10/1999 | Harvey et al. | |
| 5,983,059 | A * | 11/1999 | Oka | G03G 15/0894 222/546 |
| 6,230,944 | B1 * | 5/2001 | Castellano | B65D 47/243 222/481.5 |
| 6,598,474 | B2 | 7/2003 | Purpura et al. | |
| 6,660,233 | B1 * | 12/2003 | Coassin | B01J 19/0046 422/564 |
| 8,273,304 | B2 | 9/2012 | Coassin et al. | |
| 2004/0265186 | A1 * | 12/2004 | Clark | B01D 61/18 422/400 |
| 2009/0186401 | A1 * | 7/2009 | Remacle | C12Q 1/6837 435/287.1 |
| 2010/0190197 | A1 * | 7/2010 | Martin | B01L 3/50255 435/29 |
| 2010/0233034 | A1 * | 9/2010 | Olivier | B01L 3/50255 422/534 |
| 2011/0091930 | A1 * | 4/2011 | Vacanti | C12M 25/04 435/33 |
| 2011/0143968 | A1 | 6/2011 | Chen et al. | |
| 2012/0028296 | A1 | 2/2012 | Poll et al. | |
| 2012/0252109 | A1 * | 10/2012 | Janetzko | B01L 3/508 435/287.2 |
| 2012/0322052 | A1 | 12/2012 | Halverson et al. | |

OTHER PUBLICATIONS

European Examination Report dated Jan. 18, 2018 issued in corresponding European Application No. 14851469.8-1101.

* cited by examiner

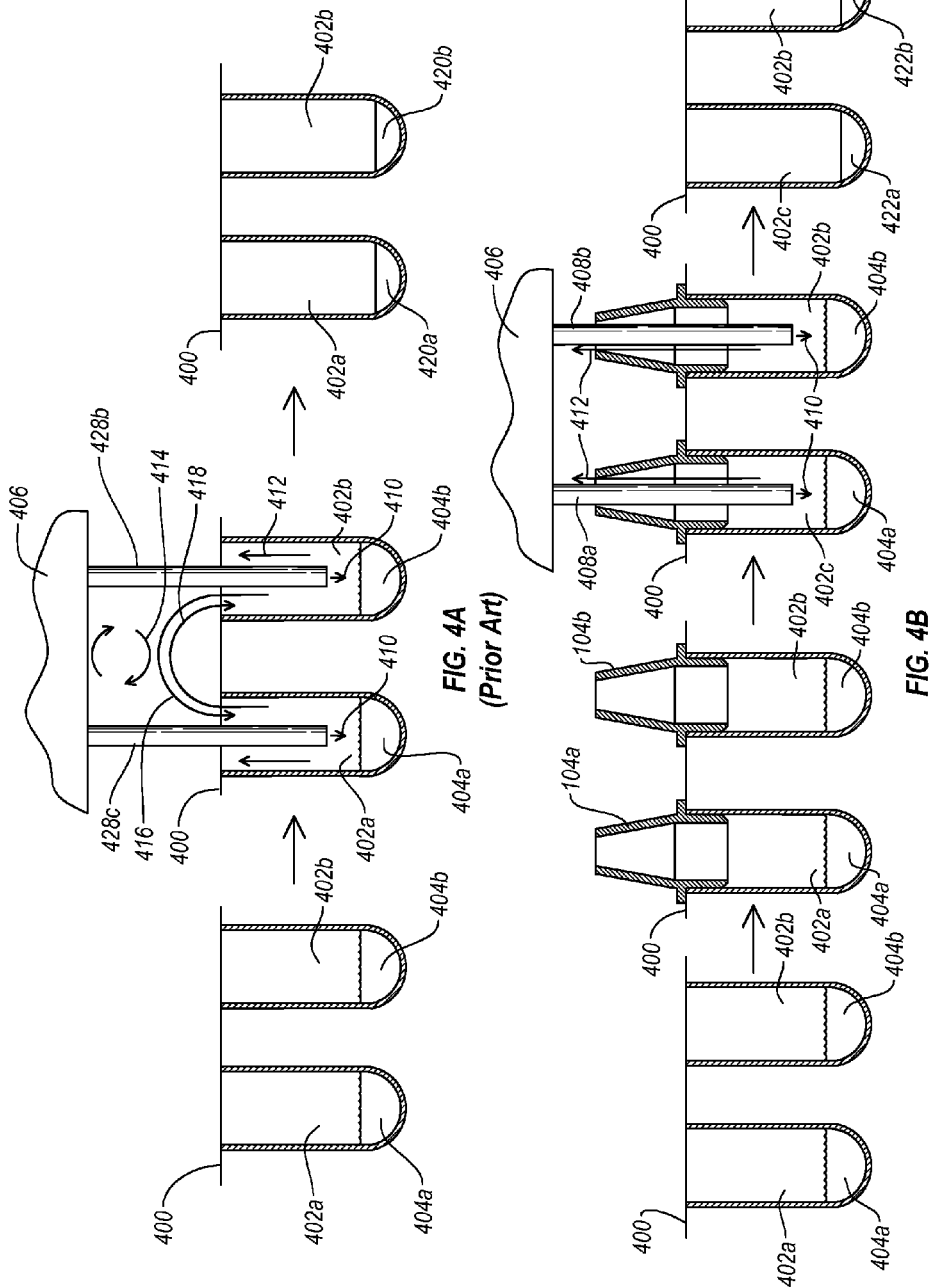

SAMPLE TUBE ADAPTERS AND METHODS OF USE THEREOF

CROSS-REFERENCE TO RELATED APPLICATION

This application claims priority to and the benefit of U.S. Provisional Application No. 61/888,993, filed on Oct. 9, 2013, entitled SAMPLE TUBE ADAPTERS AND METHODS OF USE THEREOF, which is incorporated herein in its entirety.

BACKGROUND

In all areas of laboratory testing, the clinical laboratory must ensure proper quality measures are in place to reduce or eliminate carryover between samples, false positive, and false negative results. Some testing techniques are generally assumed to be better than others (e.g., less prone to yielding false positive and false negative results). For example, quantitative, confirmatory testing using liquid chromatography-tandem mass spectrometry is often taken at face value to be more specific than qualitative, antibody-based detection methods, but this is not always true.

The transition from individual vial to 96-well based, high-throughput sample preparation methods is one of many examples of the progress in clinical laboratory testing. Samples can be processed more rapidly and many automated systems have been developed for processing 96-well plates. Nevertheless, small sample volumes and the small form factor of 96-well plates may increase the likelihood of false-positive results for wells in close proximity to significantly elevated wells. For example, an increased likelihood of false-positive results for wells in close proximity to significantly elevated wells at a rate of approximately 4% has been observed in mass-spectrometry analysis of drugs of abuse using a 96-well format. Error rates may be expected to increase as high-throughput assays are transitioned to plates having a greater number of wells (e.g., 384 well plates or even 1536 well plates).

BRIEF SUMMARY

Described herein are sample tube adapters dimensioned to fit into one or more sample tubes in order to prevent carryover or contamination between sample tubes that are adjacent to one another during one or more stages of sample preparation. Methods for use of such sample tube adapters and methods for preventing carryover or contamination between sample tubes that are prepared adjacent to one another are also described. The sample tube adapters described herein were developed to mitigate or eliminate cross-well contamination identified in high-throughput assays, e.g., 96-well based assays. In one embodiment, the sample tube adapters are designed to fit onto the top of a standard 96-well plate and are kept in place during one or more stages of sample preparation, e.g., a forced-air dry-down portion of sample preparation.

The inventor has found that there is a tendency for samples having an elevated concentration of a selected analyte to cross-contaminate their neighbors when samples are prepared in close proximity to one another. The design of the sample tube adapters described herein mitigates or eliminates this problem by providing narrowed exit sites at the top of each well. The narrowed exit sites provide a narrowed exit path for volatile solvents, which increases the velocity at which the gas phase solvent exits the well and reduces the probability of well-to-well contamination. Similarly, the narrowed top provided by the sample tube adapters described herein lessens the likelihood that cross-contamination will occur through splashing or material falling into the tubes. As such, the sample tube adapters and methods described herein are designed to mitigate the risk of reporting false positive results for true negatives that are prepared in close proximity to samples having an elevated concentration of a selected analyte.

In an embodiment, a sample tube adapter dimensioned to fit into one or more sample tubes in order to prevent carryover or contamination between sample tubes that are adjacent to one another during one or more stages of sample preparation is described. The sample tube adapter includes an open proximal end defined by a first member dimensioned to be inserted into a sample tube, a tapered member that tapers distally from a first width adjacent to the first member to a second smaller width at a distal end of the sample tube adapter, and an open distal end providing a narrowed exit site defined by the tapered member, wherein the open distal end is dimensioned to allow gases to escape from the sample tube with increased velocity without buildup of pressure inside the sample tube.

In another embodiment, an apparatus dimensioned to fit onto a multi-well format plate is described. The apparatus includes an array of sample tube adapters arranged on a structure (e.g., a mat) having a bottom surface and a top surface. The bottom surface of the structure includes a plurality of separate open ended first members dimensioned to fit into a corresponding plurality of sample tubes of the multi-well format plate, and the top surface of the structure includes a plurality of separate second members in fluid communication with each of the first members. Each second member includes a tapered portion that that tapers distally from a first width adjacent to a first member to a second smaller width at a distal end of the second member, and an open distal end providing a narrowed exit site defined by the tapered portion. The open distal end is dimensioned to allow gases to escape from a sample well of the multi-well format plate with increased velocity without buildup of pressure inside the sample well. In one embodiment, the apparatus is dimensioned and configured to fit onto one of a 6, 12, 24, 48, 96, 384, or 1536 well plate. While 6, 12, 24, 48, 96, 384, and 1536 well plates are specifically mentioned, one will appreciate that the sample tube adapters described herein can be dimensioned and configured to fit other plate sizes and well numbers.

In yet another embodiment, a kit is described. The kit includes a multi-well format plate and an apparatus, as described in greater detail elsewhere herein, that includes a plurality of sample tube adapters dimensioned to fit onto the multi-well format plate and prevent cross contamination between wells of the multi-well format plate.

In still yet another embodiment, a method for preventing cross-contamination between samples prepared in close proximity to one another is described. The method includes (1) providing at least two sample tubes, wherein each of the at least two sample tubes includes a sample to be analyzed, (2) fitting an apparatus into each of the at least two sample tubes, the apparatus being configured for preventing cross-contamination between each of the at least two tubes, and (3) with the apparatus in place, performing at least one sample preparation step to prepare the samples to be analyzed for analysis. In one embodiment, the at least one sample preparation step includes a forced air dry down step for removing a volatile solvent from each of the samples to be analyzed.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which:

FIG. 4A illustrates a prior art method for preparing samples for analysis;

FIG. 4B illustrates a method for preparing samples for analysis, according to an embodiment of the present disclosure;

DETAILED DESCRIPTION

I. Introduction

Figure 1A:
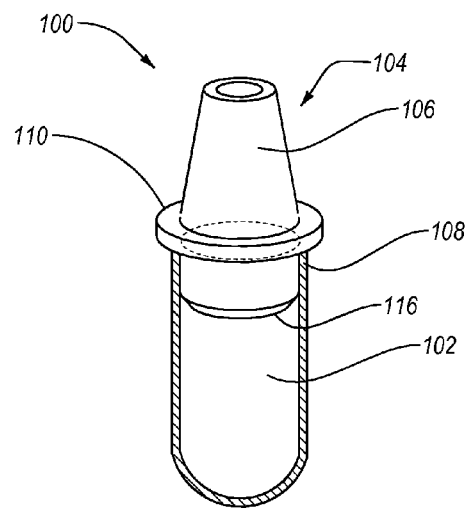
FIG. 1A is a perspective view illustrating a sample tube and a sample tube adapter configured to mitigate cross-contamination, according to an embodiment of the disclosure.

Described herein are sample tube adapters dimensioned to fit into one or more sample tubes in order to prevent carryover or contamination between sample tubes that are adjacent to one another during one or more stages of sample preparation. Methods for use of such sample tube adapters and methods for preventing carryover or contamination between sample tubes that are prepared adjacent to one another are also described. The sample tube adapters described herein were developed to mitigate or eliminate cross-well contamination identified in high-throughput assays, e.g., 96-well based assays. In one embodiment, the sample tube adapters are designed to fit onto the top of a standard 96-well plate and are kept in place during one or more stages of sample preparation, e.g., a forced-air dry-down portion of sample preparation.

The inventor has found that there is a tendency for samples having an elevated concentration of a selected analyte to cross-contaminate their neighbors when samples are prepared in close proximity to one another. The design of the sample tube adapters described herein mitigates or eliminates this problem by providing narrowed exit sites at the top of each well. The narrowed exit sites provide a narrowed exit path for volatile solvents, which increases the velocity at which the gas phase solvent exits the well and reduces the probability of well-to-well contamination. Similarly, the narrowed top provided by the sample tube adapters described herein lessens the likelihood that cross-contamination will occur through splashing or material falling into the tubes. As such, the sample tube adapters and methods described herein are designed to mitigate the risk of reporting false positive results for samples that are prepared in close proximity to samples having an elevated concentration of a selected analyte.

While high throughput systems have been a real boon to clinical testing laboratories, these methods do carry risks. For example, because these samples are prepared in large batches, they are subject to systematic errors and random errors in sample preparation and processing. Likewise, the reduced form factor of high throughput plates and preparation equipment increases the likelihood that cross-contamination will occur as a result of proximity. In addition, because the technician's connection to any individual sample is reduced, the tracking of errors can be difficult.

The sample tube adapters and associated methods described herein provide a means for mitigation and or prevention of cross-contamination between samples prepared in close proximity to one another and especially for samples processed and/or assayed in a sample array format (e.g., in a high throughput environment). As used herein, the term "sample array" refers to a set of samples that are prepared and/or run as a batch in a multi-well format (e.g., a 96 well plate).

In one example, the inventor has found that true negative samples for a given analyte are more likely to be assayed as positives when they are prepared and assayed in close proximity to samples with extremely high positive values for the given analyte. These samples with extremely high positive values for one or more given analytes are referred to as "hotspots." The concentration of one or more given analytes is so high in a "hotspot" that even a very small amount of carryover (e.g., about 0.1-0.3%) from the hotspot to a neighboring sample would be sufficient to cause the neighboring negative sample to come up positive. What constitutes an "extremely high positive value" will depend to some extent on the concentration range of the analyte and on the limit of detection. In one embodiment, the sample tube adapters and methods described herein provide a means for reducing the risk of reporting a false positive as a result of cross-contamination between highly elevated positive samples (referred to herein as "hotspots") and true negative samples in an environment where samples are prepared and/or assayed in close proximity to one another, such as in a high throughput environment.

II Sample Tube Adapters

Figure 1B:
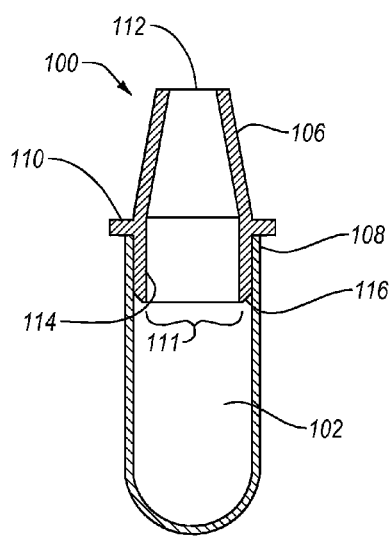
FIG. 1B illustrates a cross-sectional view of the sample tube adapter of FIG. 1A.

The following discussion now refers to a number of configurations for sample tube adapters that are dimensioned to fit into one or more sample tubes in order to prevent carryover or contamination between sample tubes. FIG. 1A is a perspective view of an assembly 100 illustrating a sample tube 102 and a sample tube adapter 104 that is dimensioned to fit into sample tube 102 and is configured to mitigate cross-contamination. FIG. 1B illustrates a cross-sectional view of the sample tube 102 and the sample tube adapter 104 of FIG. 1A. The sample tube 102 may be any type of sample tube used in a laboratory for preparing samples for analysis or testing. Examples include, but are not limited to, test tubes (glass or plastic), Eppendorf tubes, conical centrifuge tubes, and the like. The sample tube 102 may also be a tube included in a multi-well format plate, such as a 6, 12, 24, 48, 96, 384, or 1536 well plate. In the illustrated embodiment, the sample tube 102 has a substantially round horizontal profile and the tube adapter 104 is configured to fit the profile of the tube 102. However, tubes having other profiles such as square, rectangular, hexagonal, oval shaped, and the like.

Referring more specifically to the sample tube adapter 104, the adapter 104 includes an open proximal end 111 defined by a first member 114 dimensioned to be inserted into the sample tube 102. Typically, the first member 114 is dimensioned to fit securely into the into the sample tube 102. As will be explained in greater detail below, in the present embodiment, it is important that the first member 114 fit securely into the sample tube so that gases are not able to escape from the sample tube 102 around the side of the first member 114. In one embodiment, the first member includes a chamfered outer edge 116 configured to facilitate insertion of the first member into a sample tube.

Additionally, sample tube adapter 104 includes a tapered member 106 that that tapers distally from a first width adjacent to the first member 114 to a second smaller width at a distal end of the sample tube adapter 104. Additionally, the sample tube adapter in the illustrated embodiment includes a flange member 110 that is positioned on the sample tube adapter 104 between the first member 114 and the tapered member 106. In one embodiment, the flange member 110 may be dimensioned to rest on the top edge 108 of a sample tube 102 to prevent the sample tube adapter 104 from falling into the sample tube 102. In addition, the flange member may improve the seal between the sample tube 102 and the sample tube adapter 104.

The distal end of the sample tube adapter 104 defines an open distal end 112 that provides a narrowed exit site defined by the tapered member. In one embodiment, the open distal end 112 is dimensioned to readily accept a probe dryer of a forced air drydown apparatus so that gases (e.g., gas from the forced air drydown apparatus and evaporated solvent from the sample) can readily escape without pressure buildup in the sample tube 102. Forced air drydown apparatuses having straight probe dryer probes are known by persons having skill in the art. For example, typical forced air drydown apparatuses can be purchased from Porvair Sciences Limited, Surrey, UK.

Figure 1C:
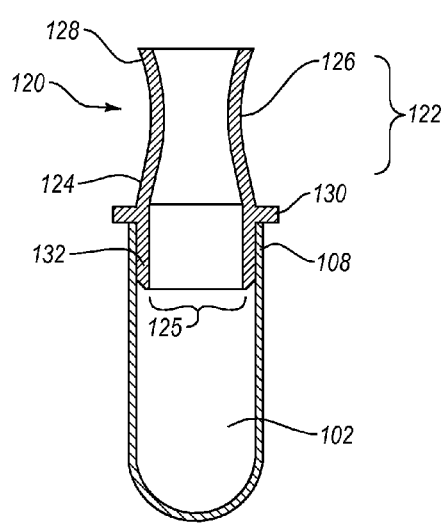
FIG. 1C illustrates a cross-sectional view of another embodiment of a sample tube adapter.

Referring now to FIG. 1C, another embodiment of a sample tube adapter 120 is illustrated. The sample tube adapter 120 is shown positioned on a sample tube 102. The sample tube adapter 120 is similar to the sample tube adapter 104 discussed above. The sample tube adapter 120 includes an open proximal end 125 defined by a first member 132 dimensioned to be inserted into the sample tube 102. Additionally, the sample tube adapter 120 includes a flange member 130 that is positioned on the sample tube adapter 120 adjacent to the first member 132.

In the illustrated embodiment, the sample tube adapter 120 includes a tapered member 122 that includes first 124 and second 128 tapered portions. The first tapered portion 124 tapers distally from a first width adjacent to the first member 132 to a second smaller width 126 near the distal end of the sample tube adapter 120. The second tapered portion 128 tapers outwardly from the second smaller width 126 and extends further distally to a third larger width from the second smaller width. In one embodiment, the third larger width is less than the first width.

The first tapered portion 124 and the second tapered portion 128 combine to give the tapered portion 122 of the sample tube adapter 120 a substantially hourglass shape. The second smaller width 126 near the distal end of the sample tube adapter 120 defines a waist portion that provides a narrowed exit site from the sample tube adapter to increase the velocity of gases exiting the sample tube 102 and the sample tube adapter, while the second tapered portion 128 is designed to facilitate insertion of a probe dryer of a forced air drydown apparatus through the distal end of the sample tube adapter 120.

Figure 1D:
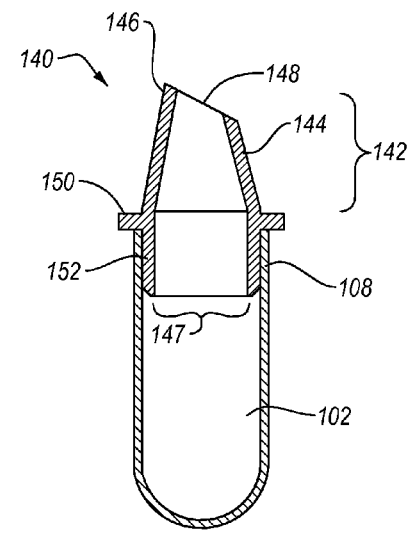
FIG. 1D illustrates a cross-sectional view of another embodiment of a sample tube adapter.
Figure 2A:
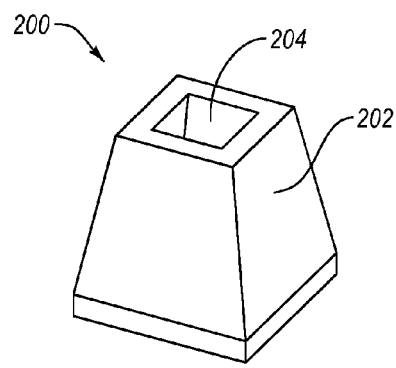
FIG. 2A illustrates a tube adapter having a square profile, according to an embodiment of the disclosure.
Figure 2B:
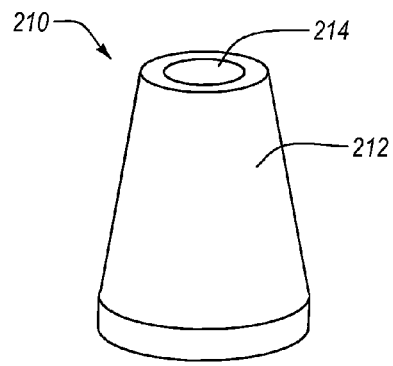
FIG. 2B illustrates a tube adapter having a substantially circular profile, according to an embodiment of the disclosure.
Figure 2C:
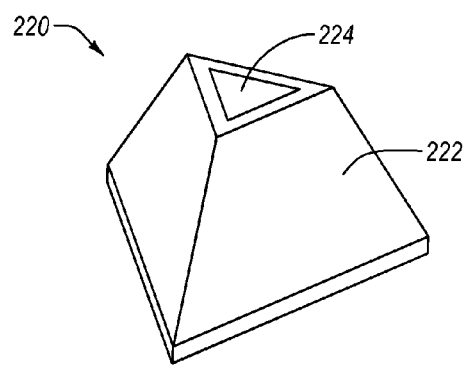
FIG. 2C illustrates a tube adapter having a triangular profile, according to an embodiment of the disclosure.
Figure 2D:
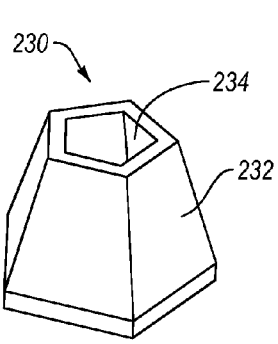
FIG. 2D illustrates a tube adapter having a pentagonal profile, according to an embodiment of the disclosure.
Figure 2E:
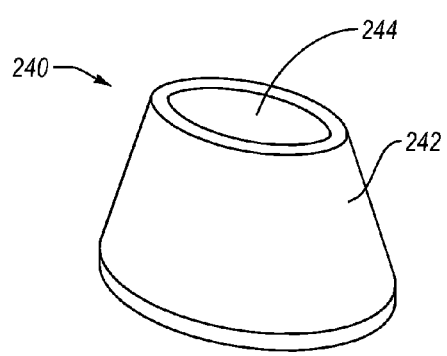
FIG. 2E illustrates a tube adapter having a oval shaped profile, according to an embodiment of the disclosure.

Referring now to FIG. 1D, another embodiment of a sample tube adapter 140 is illustrated. The sample tube adapter 140 is shown positioned on a sample tube 102. The sample tube adapter 140 is similar to the sample tube adapter 104 discussed above. The sample tube adapter 140 includes an open proximal end 147 defined by a first member 152 dimensioned to be inserted into the sample tube 102. Additionally, the sample tube adapter 140 includes a flange member 150 that is positioned on the sample tube adapter 140 adjacent to the first member 152.

In the illustrated embodiment, the sample tube adapter 140 includes a tapered member 142 that includes a first half 146 and a second half 144 that define an asymmetrical opening 148 at the distal end of the sample tube adapter 140. The tapered portion 142 tapers distally from a first width adjacent to the first member 152 to a second smaller width at the distal end of the sample tube adapter 140 to define the asymmetrical opening.

The asymmetrical opening 148 may accommodate insertion of a probe dryer of a forced air drydown apparatus through the distal end of the sample tube adapter 140 as in the previous examples. Additionally, the asymmetrical opening 148 may be configured to accommodate side entry of a probe dryer of a forced air drydown apparatus. For example, Turbovap brand forced air drydown apparatuses, which are made by Biotage AB of Uppsala, Sweden, include probes that enter from the side.

In one embodiment, the sample tube adapters discussed above may be fabricated from materials such as, but not limited to, one or more of metal, polypropylene, polyethylene, polycarbonate, silicone, silicone rubber, thermo-plastic polymers, or neoprene rubber. Likewise, the sample tube adapters discussed above may be fabricated for one time use or they may be configured for multiple use cycles.

Referring now to FIGS. 2A-2E, sample tube adapters having a number of different shapes are illustrated. As discussed above, the portion of the sample tube adapter that is designed to fit into a sample tube can have a number of different shapes depending on the shape of the tube that the sample tube adapter is designed to fit. Likewise, the tapered portion can have a number of shapes depending on a number of factors. For example, the tapered portion may follow the shape of the portion of the sample tube adapter that is designed to fit into a sample tube, or the tapered portion may have a shape selected on the basis of aesthetics or a shape that makes efficient use of space when sample tubes are arranged in an array. In the embodiments illustrated in FIGS. 2A-2E, an adapter with a square pyramidal profile (200), a round conical profile (210), a trigonal pyramidal (220), pentagonal pyramidal, and oval shaped cone (240) are illustrated. One will appreciate, however, that these shapes are merely illustrative and that other shapes are possible and within the scope of this disclosure.

In one embodiment, more than one of the sample tube adapters illustrated herein may be arranged to fit into at least two sample tubes that are positioned in close proximity to one another (e.g., next to each other). For example, such sample tube adapters may include at least two separate first members and tapered members interconnected into a structure configured to fit the at least two separate first members into a corresponding at least two sample tubes. In another embodiment, multiple sample tube adapters may be arranged in an array to be fitted into a corresponding array of sample tubes. For example, sample tube adapters may be arranged in an array to fit into a corresponding array of sample tubes. Such a structure may be configured to fit the plurality of separate first members into each of the sample tubes of a multi-well format plate such as one of a 6, 12, 24, 48, 96, 384, or 1536 well plate.

Figure 3A:
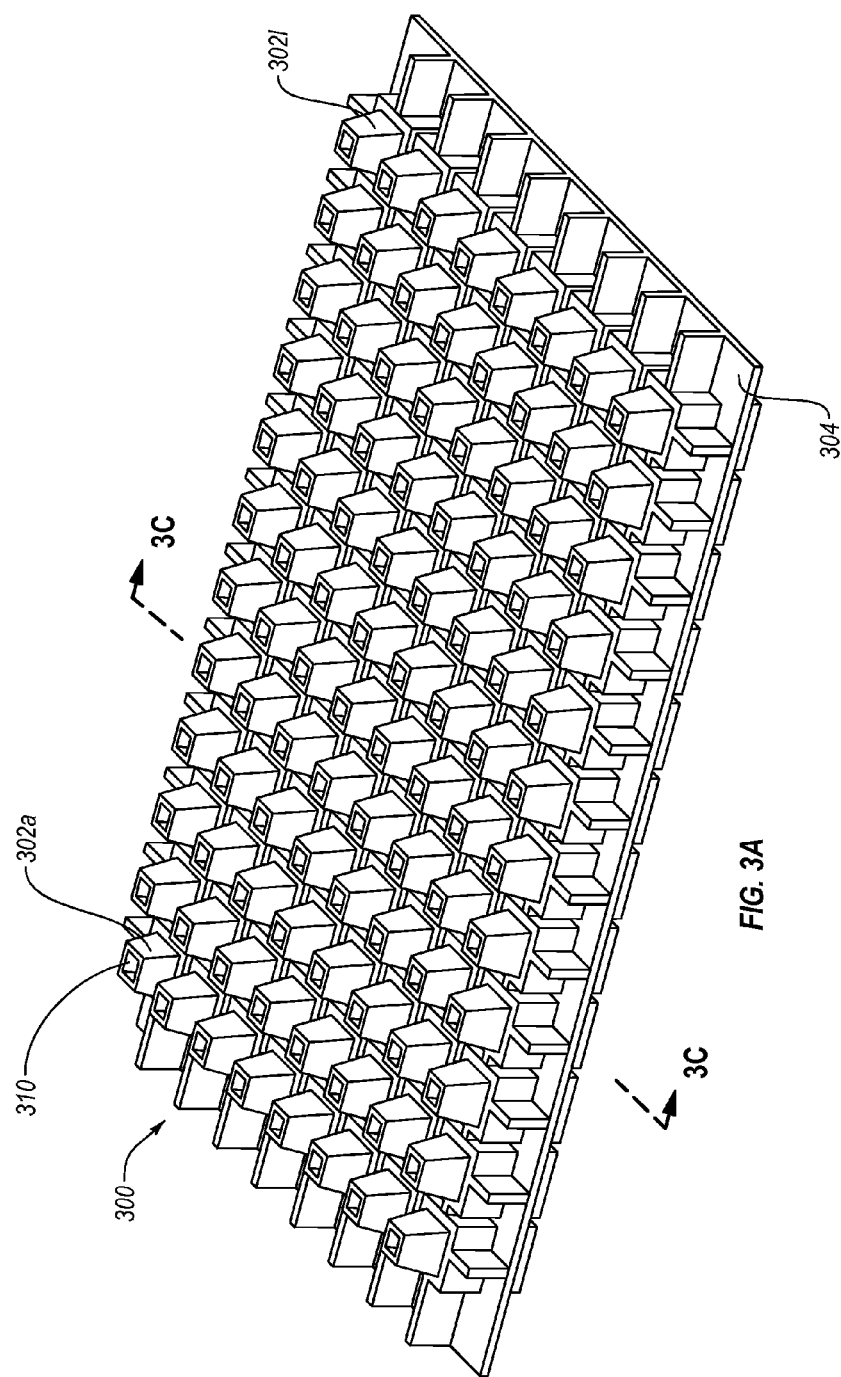
FIG. 3A illustrates a perspective view of a top side of a sample mat dimensioned to fit onto a multi-well format plate, according to an embodiment of the disclosure.
Figure 3B:
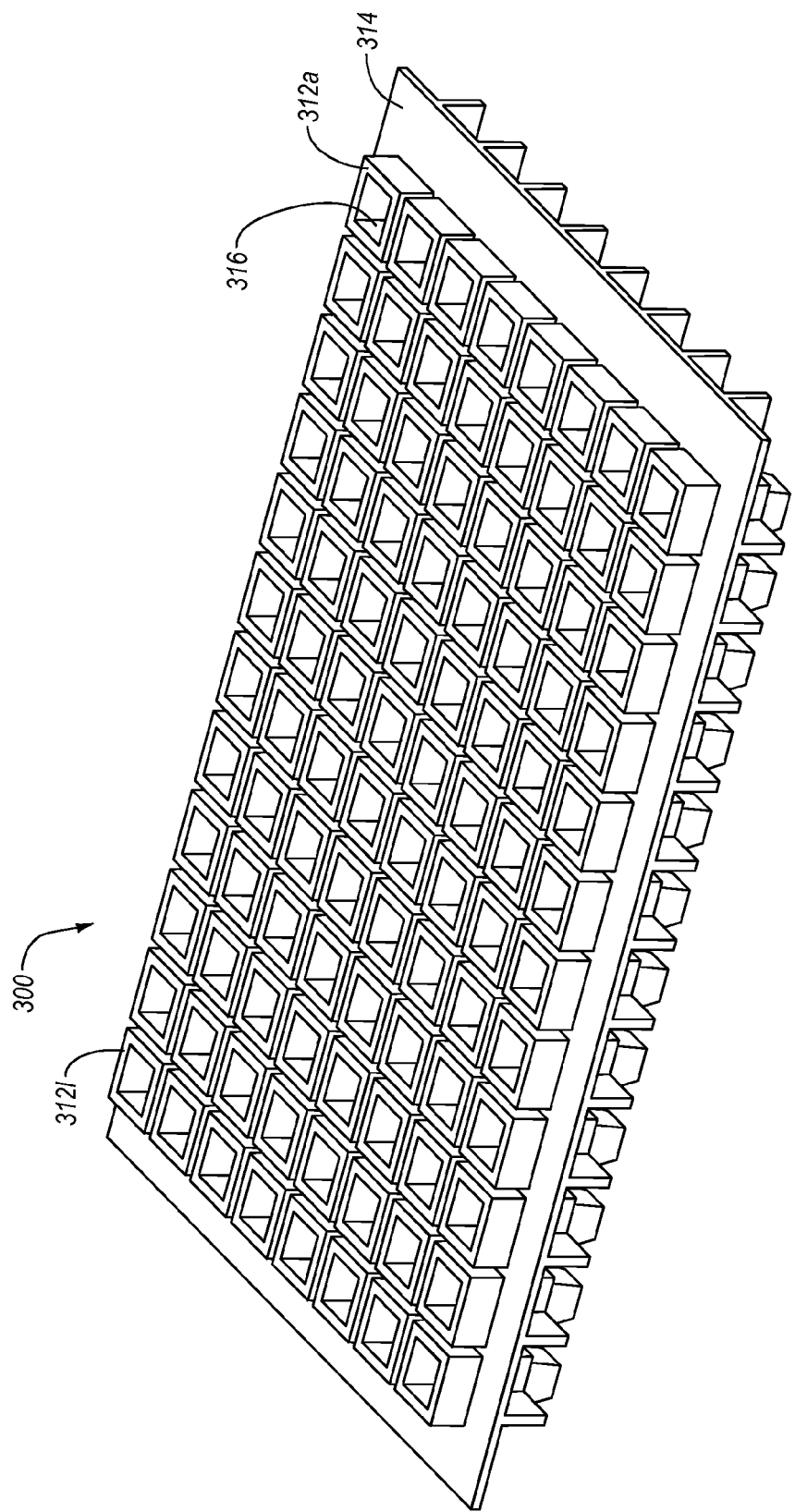
FIG. 3B illustrates a perspective view of a bottom side of a sample mat dimensioned to fit onto a multi-well format plate, according to an embodiment of the disclosure.
Figure 3C:
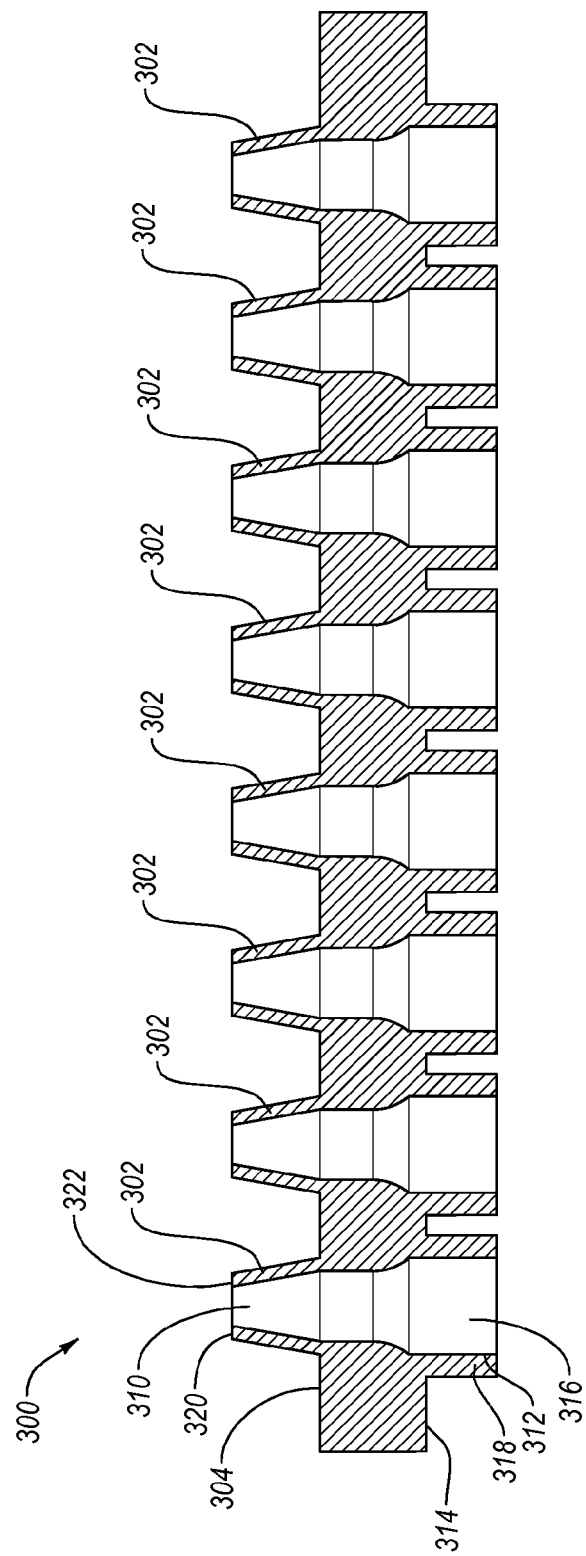
FIG. 3C illustrates a side cut-away view of the sample mat of FIGS. 3A and 3B.

Referring now to FIGS. 3A-3C, an apparatus 300 that is configured and dimensioned to fit onto a multi-well format plate is illustrated. The apparatus 300 includes a an array of sample tube adapters that are spaced and dimensioned such that each adapter may be fitted into a sample well of a multi-well format plate, such as one of a 6, 12, 24, 48, 96, 384, or 1536 well plate.

In one embodiment, the apparatus 300 includes a structure (e.g., a mat) having a top surface 304 and a bottom surface 314. The bottom surface of the apparatus 300 includes a plurality of separate open ended 316 first members 312 dimensioned to fit into a corresponding plurality of sample tubes of the multi-well format plate. In the illustrated embodiment, the apparatus 300 is configured to fit to a 96-well plate. Thus, the bottom surface 314 of the apparatus 300 includes 96 first members configured to fit into each of the 96 wells of a 96-well plate. First members 312*a*-312*l* are illustrated for reference.

The top surface 304 of the apparatus 300 includes a corresponding plurality of separate second members 302 that are in fluid communication with each of the first members 312. As can be seen in the cross sectional view shown in FIG. 3C, each second member 302 includes a tapered portion 310 that that tapers distally from a first width adjacent to a first member 312 to a second smaller width at a distal end 320 of the second member 302. Each second member 302 further includes an open distal end 322 providing a narrowed exit site defined by the taper, wherein the open distal end 322 is dimensioned to allow gases to escape from a sample tube with increased velocity without buildup of pressure inside the sample tube.

As in the examples described above, the open distal end 322 of each of the second members 302 is, in the present embodiment, dimensioned to accommodate a probe of a forced air dryer apparatus while allowing gases to escape from the sample tube without buildup of pressure inside the sample tube. In one embodiment, the open distal end 322 is dimensioned to accommodate top down entry of the probe of a forced air dryer apparatus. In another embodiment, the open distal end 322 is dimensioned to accommodate side entry of the probe of a forced air dryer apparatus.

In one embodiment, the present invention may include a kit for preparing samples for assay in a multi-well format. The kit may include a multi-well format plate and an apparatus (e.g., apparatus 300) as described herein having a plurality of separate sample tube adapters configured to fit into each of the sample wells of the multi-well format plate and thereby isolate the sample wells from one another to prevent cross contamination between sample wells during one or more sample preparation steps.

In one embodiment, the apparatus may include a bottom surface and a top surface, the bottom surface being dimensioned to fit onto the multi-well format plate. The bottom surface of the apparatus includes a plurality of separate open ended first members dimensioned to fit into a corresponding plurality of sample tubes of the multi-well format plate. The top surface of the apparatus includes a plurality of separate second members in fluid communication with each of the first members, each second member including: a tapered portion that that tapers distally from a first width adjacent to a first member to a second smaller width at a distal end of the second member, and an open distal end providing a narrowed exit site defined by the taper, wherein the open distal end is dimensioned to allow gases to escape from a sample tube with increased velocity without buildup of pressure inside the sample tube.

In one embodiment, the kit includes one or more of a 6, 12, 24, 48, 96, 384, or 1536 well plate and apparatus(es) configured to fit the well-plate(s) included in the kit.

II Methods for Sample Tube Preventing Cross-Contamination Between Samples

In one embodiment, a method for preventing cross-contamination between samples prepared in close proximity to one another is described. However, to better describe the method claimed herein, a prior art method will first be described in reference to FIG. 4A.

The prior at method includes providing at least two sample tubes 402*a* and 402*b* that each contain a sample to be analyzed 404*a* and 404*b*. The samples tubes 402*a* and 402*b* and the samples therein 404*a* and 404*b* are prepared for analysis in close proximity to one another and are therefore subject to a risk of cross-contamination between the contents of the sample tubes.

As part of the prior art method illustrated in FIG. 4A, the samples 404*a* and 404*b* are dried down to concentrate the samples 404*a* and 404*b* and to remove the solvent from prior preparation steps. To dry the samples 404*a* and 404*b*, a first probe 408*a* and a second probe 408*b* of a forced air drydown apparatus 406 are lowered into the sample tubes 402*a* and 402*b* and a stream of gas 410 (e.g., dry nitrogen) is passed over the samples 404*a* and 404*b*. The action of the stream of gas 410 causes the solvent in the samples 404*a* and 404*b* to evaporate and flow out of the tube, which is represented by arrows 412. However, the inventor in this case has observed that in the evaporation process some of the analyte can be carried out of the tube along with the solvent 412. When samples that contain a highly elevated concentration of an analyte are prepared adjacent to negative samples, a small amount of carryover (e.g., about 0.1-0.3%) from the highly elevated sample to the adjacent negative can be enough to produce a false positive.

While the exact mechanism of this cross contamination is unknown, without being tied to one theory, it is possible that an eddy current 416 may form during the evaporation process, which may case cross-contamination (represented by arrows 416 and 418) between samples. Such cross contamination may, for example, result in the reporting of a false positive from either dried down sample 420a or 420b.

Referring now to FIG. 4B, a method claimed herein that uses the sample adapters described herein is illustrated. The method includes (1) providing at least two sample tubes 402a and 402b that each contain a sample to be analyzed 404a and 404b. In the illustrated embodiment, the samples tubes 402a and 402b are part of a structure 400. Such a structure 400 may, for example, include a 96-well plate.

The method further includes (2) fitting an apparatus 104a and 104b into tubes 402a and 402b to prevent cross-contamination between each of the at least two tubes 402a and 402b. With the apparatuses 104a and 104b in place, the method further includes (3) performing at least one sample preparation step to prepare the samples to be analyzed for analysis. In the illustrated embodiment, the at least one sample preparation step includes a forced air dry down step to remove a volatile solvent from each of the samples to be analyzed.

To dry the samples 404a and 404b, a first probe 408a and a second probe 408b of a forced air drydown apparatus 406 are lowered into the sample tubes 402a and 402b and a stream of gas 410 (e.g., dry nitrogen) is passed over the samples 404a and 404b. The action of the stream of gas 410 causes the solvent in the samples 404a and 404b to evaporate and flow out of the tube, which is represented by arrows 412. However, in contrast to the prior art method described above, it has been observed by the inventor in this case that the sample tube adapters 104a and 104b prevent or significantly mitigate contamination between sample tubes 402a and 402b.

Without being tied to one theory, it is believed that the sample tube adapters described herein (e.g., sample tube adapters 104a and 104b) increase the velocity of the gases exiting the sample tubes so that the solvent and any analyte that may be contained therein is carried safely away from adjacent sample tubes. And even if an eddy current or a similar air current were to form, the sample tube adapters described herein reduce the surface area of the top of the tubes, which lessens the likelihood that material could reenter the tubes from adjacent tubes. In contrast to the prior art situation, dried samples 422a and 422b are much less likely to be cross-contaminated and, as such, the risk of reporting a false positive is significantly reduced.

EXAMPLES

Example I

Validation of the Sample Tube Adapter

Figure 5:
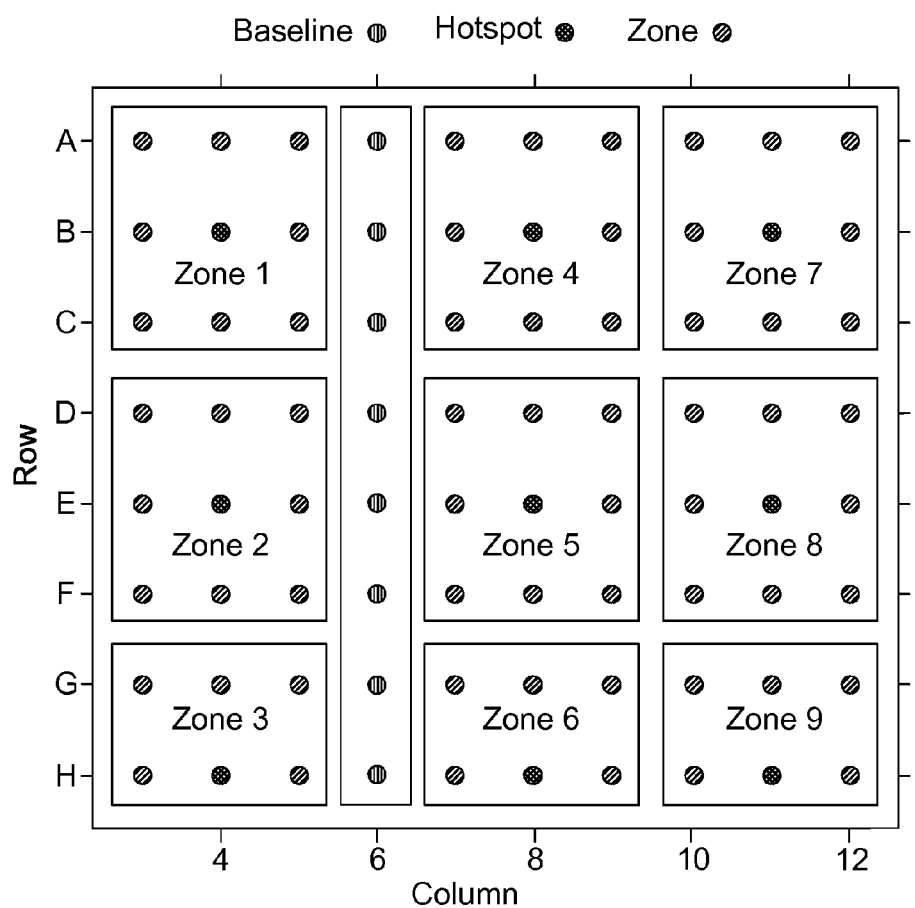
FIG. 5 schematically illustrates a plate setup of a multi-well format plate for a plate adapter validation experiment.

The following example illustrates the validation of the sample tube adapters described herein. Validation of the sample tube adapter was done according to FIG. 5. Nine "hotspot" zones were created by spiking urine with 6000 ng/ml of each of oxymorphone, hydromorphone, morphine, oxycodone, 6-AM, codeine, and hydrocodone; 6000 ng/ml is a value consistent with highly elevated patient results encountered in the clinical laboratory for these drugs. Wells surrounding the hotspots were spiked at 25 ng/mL of the drugs of interest. In addition, baseline vales for each of the drugs of interest were established by spiking clean urine with 25 ng/mL of the drugs of interest. Contamination of wells in proximity to the "hotspots" with and without the sample tube adapters was investigated for urine LC-MS/MS assays designed to detect oxymorphone, hydromorphone, morphine, oxycodone, 6-AM, codeine, and hydrocodone.

Confirmation testing for the drugs listed above utilizes similar sample preparation procedures including: solid phase extraction using 96-well Phenomenex Strat X-C solid phase preassembled plates. The samples were dried down prior to mass-spec analysis similar to the procedure described above with reference to FIGS. 4A and 4B. Chromatographic separation and analysis using multiple reaction monitoring was conducted using a Waters Acquity Ultra performance LC-MS/MS system equipped with a Waters Acquity UPLC system, Acquity HSS C18 UPLC 1.8 µm particle size, 2.1×50 mm analytical column and ESCI probe in positive electrospray ionization mode.

Figure 6A:
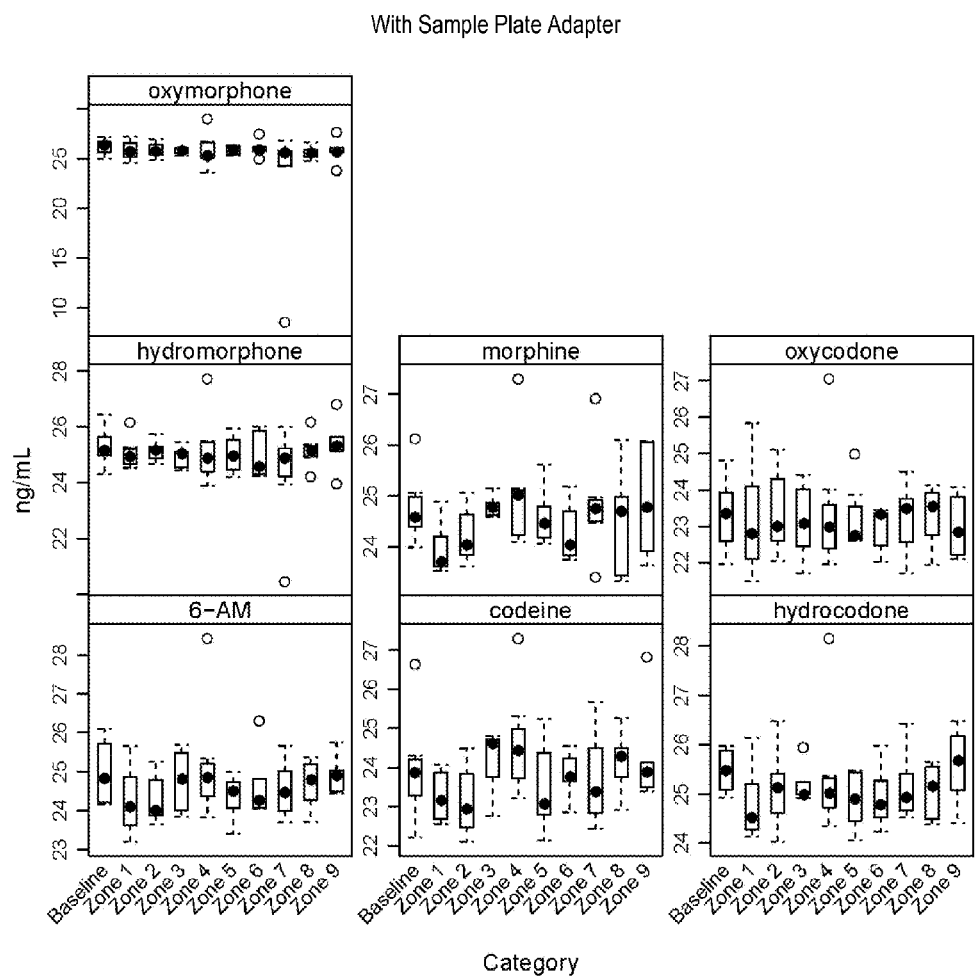
FIG. 6A illustrates the results of mass-spec analysis of low concentration samples surrounding the nine hotspots indicated in the plate setup illustrated in FIG. 5 prepared with an embodiment of the plate adapter illustrated herein.
Figure 6B:
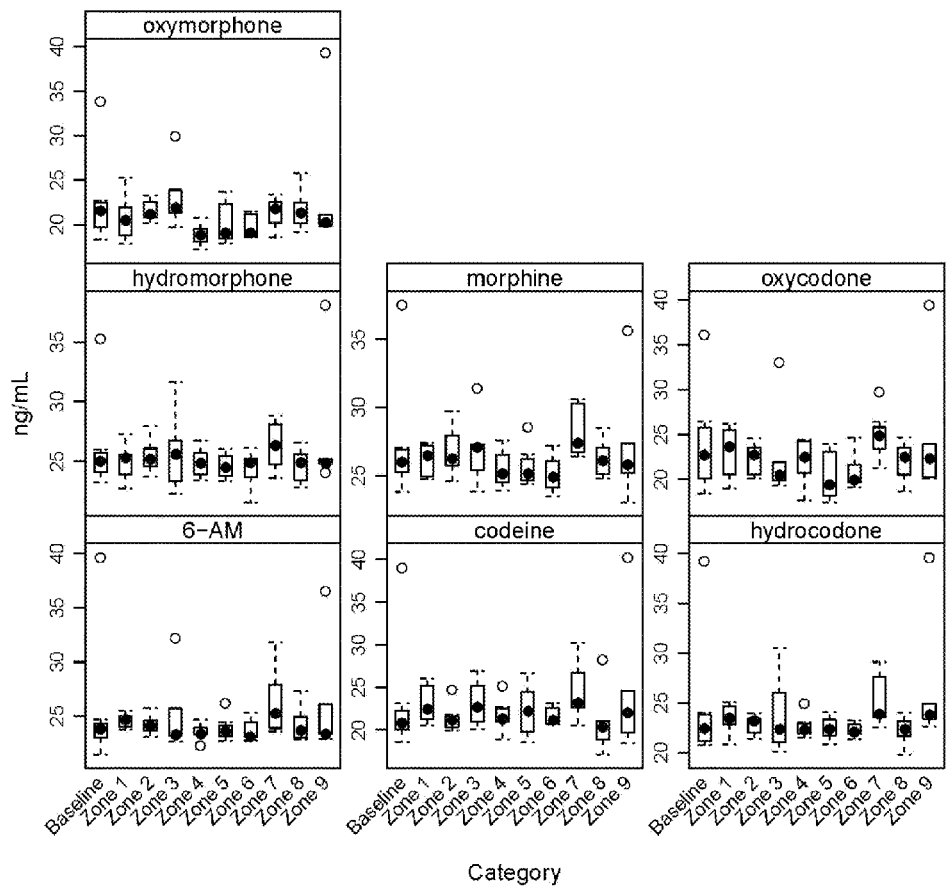
FIG. 6B illustrates the results of mass-spec analysis of low concentration samples surrounding the nine hotspots indicated in the plate setup illustrated in FIG. 5 prepared without a plate adapter.

The distribution of results for the surrounding wells in each zone was plotted as seen in FIGS. 6A and 6B. FIG. 6A shows the distribution of results for each of the drugs of interest around the hotspots with the use of the plate adapter. FIG. 6B shows the distribution of results for each of the drugs of interest around the hotspots without the use of the plate adapter. The acceptable imprecision for the values in each zone if no well-to-well contamination occurred is expected to be consistent with the inter-assay imprecision of the individual assays or approximately 10-20% (e.g., 15% or less).

As can be seen in FIG. 6A, the sample results where the plate adapter was used show some variation but all of the values are clustered around 25 ng/ml within the accepted variation of 10-20% or less—or an acceptable high variation of value of about 28-29 ng/ml for the sample.

In contrast, in FIG. 6B where the plate adapter was not used the sample values show a great deal of high variation in the concentration values for the assayed amounts of the drugs of interest. For the samples surrounding the hotspots, normal variation in the assay may be expected to produce a high variation of about 10-20% (e.g., 15% or less). As can be seen in FIG. 6B, many of the assayed samples greatly exceed this acceptable variation. Of note is the change of the scale of the Y-axis between FIGS. 6A and 6B. While the Y-axes of FIG. 6A all have a high end in the range of 25-30 ng/ml, the Y-axes of FIG. 6B all have a high end in the range of 35-40 ng/ml. Moreover, there are samples that exceed the 10-20% normal expected variation for each of oxymorphone, hydromorphone, morphine, oxycodone, 6-AM, codeine, and hydrocodone. It is believed that that the high outlier samples illustrated in FIG. 6B are high because of contamination from the hotspots that occurs in the absence of the plate adapter.

FIGS. 6A and 6B demonstrate the reduction in well-to-well contamination using the sample tube adapters described herein. None of the samples illustrated in FIG. 6A exceeds the acceptable high variation for detected concentration for each of the analytes. One sample for hydromorphone and one sample for hydrocodone are on the borderline of being higher than expected, but their values are generally within the acceptable limits.

Example 2

Assay for 17-Hydroxy-Pregnenolone

While sample carryover and the effect of the sample plate adapter are described in detail above in reference to opiates, sample carryover and contamination has also been observed in other assays. In one example, sample carryover was observed in an endocrinology assay for 17-hydroxy-pregnenolone. It was observed that routine carryover in that assay could be addressed with the use of the sample plate adapter described herein. For instance, prior to the use of the plate adapter the target value for the control was observed to be about 121 ng/dl. After implementing the plate adapter the mean target value shifted to about 109 ng/dl demonstrating that the samples were being contaminated on a routine basis causing a false elevation in the final result. This was evident as well by the "negative" control sample having a quantifiable amount of 17-hydroxy-pregnenolone on a routine basis. Normally, it should be zero. With the use of the plate adapter, it is routinely zero.

Example 3

Cost Savings Associated with the Use of the Sample Plate Adapter

In identifying the so-called "hotspot" carryover problem, the inventor determined that carryover from elevated samples could lead to contamination and the reporting of false positives. In essence, this problem may arise due to the fact that samples are often prepared in close proximity to one another, which increases the chances for cross-contamination. In exploring solutions to this problem, it was hypothesized that the problem could be addressed in, for example, a 96-well plate by separating the samples and only using 24 of the sample wells of the plate so that all of the "sample" wells are abutted by empty wells. This was referred to as the "checkerboard" setup. While this approach was successful, it is not without its drawbacks. This constraint resulted in dramatic increases in costs due to consumables, added technologist time, and a potentially devastating constraint on laboratory volume growth. However, it was found that the use of the sample plate adapter described herein was at least as good in terms of preventing contamination and carryover while also yielding significant cost savings and increasing laboratory throughput. The checkerboard setup and the sample plate adapter were compared according to a procedure similar to the one described in Example I.

For example, a laboratory processing 140 samples a day would require six sample preparation runs of 24 samples in a 96 well plate resulting in substantial QC material waste, wasted reagents, excess consumables and excess technologist time. In contrast, after validation of the plate adapter it was found that only two batches per day were needed. For instance, it was found that the savings in technologist time, reduction of wasted consumables, and higher throughput with the plate adapter resulted in a savings of over $13,000 in a typical month. Further, use of the plate adapter has allowed for a dramatic increase in quality that will result in reduced assay time.

Moreover, use of the plate adapter allows for increased throughput and laboratory growth. Assuming a typical increase in the number of sample tests ordered of 10% per month, a typical laboratory's capacity would be rapidly outstripped without an increase in instrumentation and the number of technologists without the use of the plate adapter.

Conclusions

Regardless of sample volume, all laboratories are increasingly interested in ways to maximize staff efficiency. The increased use of liquid chromatography-tandem mass spectrometry for clinical laboratory testing has enhanced the ability to develop high-throughput, multiplexed testing. However, such testing requires highly-skilled operators, extensive data review and varying degrees of complexity in sample preparation. As clinical mass spectrometry continues to evolve so too does our understanding of the unique challenges and needs essential to provide the expected level of quality control.

The inventor has identified a potentially underappreciated quality issue possibly affecting any 96-well based clinical assay. To ensure that laboratories can confidently report data collected in testing, the inventor has developed a sample tube adapter for use in the clinical laboratory to aid in the prevention and/or mitigation of well-to-well contamination in 96-well, high throughput LC-MS/MS assays. Use of the sample tube adapters described herein reduces the need for laborious data review by staff and has substituted a manual process with a robust method amenable to refinement and modification without requiring staff retraining.

The sample tube adapters described herein significantly reduced the well-to-well contamination previously identified and dramatically reduces the need for concern over false positives due to elevated patient samples in proximity to negative patient samples.

II—Dimensions:

Shown below in Table 1 are typical dimensions for a sample tube adapter mat that is dimensioned for fitting onto a 96-well plate.

TABLE 1

| Component | Length (mm) | Width (mm) | Height (mm) |
|---|---|---|---|
| Plate | 12 | 8 | 1.4 |
| Tapered member - base | 0.5 | 0.5 | 0.5 |
| Tapered member - top | 0.3 | 0.3 | |
| First insert | 0.6 | 0.6 | 0.3 |

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A sample tube adapter, comprising:
   an open proximal end defined by a first member configured to be inserted into a sample tube;
   a tapered member that tapers distally from a first width adjacent to the first member to a second smaller width at a distal end of the sample tube adapter; and
   an open distal end providing a narrowed exit site defined by the tapered member, wherein the open distal end is configured to allow gases to escape from the sample tube with increased velocity without buildup of pressure inside the sample tube,
   wherein the open distal end is configured to accommodate a probe of a forced air dryer apparatus while allowing gases to escape from the sample tube without buildup of pressure inside the sample tube,
   wherein the open distal end is configured to accommodate side entry of the probe of the forced air dryer apparatus.

2. The sample tube adapter of claim 1, further comprising a flange member positioned on the sample tube adapter between the first member and the tapered member and configured to rest atop the sample tube.

3. The sample tube adapter of claim 1, wherein the tapered member further comprises a distal extension that tapers outward to a third larger width from the second smaller width.

4. The sample tube adapter of claim 3, wherein the third larger width is less than the first width.

5. The sample tube adapter of claim 1, wherein the open distal end is configured to accommodate top down entry of the probe of the forced air dryer apparatus.

6. The sample tube adapter of claim 1, wherein the first member includes a chamfered outer edge configured to facilitate insertion of the first member into the sample tube.

7. The sample tube adapter of claim 1, wherein the tapered member is at least one of funnel shaped, cone shaped, a pyramidal shape having at least three sides, or hourglass shaped.

8. The sample tube adapter of claim 1, wherein the sample tube adapter is fabricated from one or more of metal, polypropylene, polyethylene, polycarbonate, silicone, silicone rubber, thermo-plastic polymers, or neoprene rubber.

9. The sample tube adapter of claim 1, wherein the sample tube adapter includes a plurality of separate first members and tapered members interconnected into a structure configured to fit the plurality of separate first members into a corresponding plurality of sample tubes.

10. The sample tube adapter of claim 9, wherein the structure is configured to fit the plurality of separate first members into each of the sample tubes of a multi-well format plate.

11. The sample tube adapter of claim 10, wherein the multi-well format plate is one of a 6, 12, 24, 48, 96, 384, or 1536 well plate.

12. The sample tube adapter of claim 1, wherein the sample tube adapter includes at least two separate first members and tapered members interconnected into a structure configured to fit the at least two separate first members into a corresponding at least two sample tubes.

13. An apparatus dimensioned to fit onto a multi-well format plate, the apparatus comprising:
an array of sample tube adapters arranged on a structure having a bottom surface and a top surface;
the bottom surface of the structure including a plurality of separate open ended first members configured to fit into a corresponding plurality of sample wells of the multi-well format plate;
the top surface of the structure including a plurality of separate second members in fluid communication with each of the plurality of separate open ended first members, each second member of the plurality of separate second members including
a tapered portion that that tapers distally from a first width adjacent to a separate first member of the plurality of separate open ended first members to a second smaller width at a distal end of the second member; and
an open distal end providing a narrowed exit site defined by the tapered portion, wherein the open distal end is configured to allow gases to escape from a sample well of the multi-well format plate with increased velocity without buildup of pressure inside the sample well.

14. The apparatus of claim 13, wherein the multi-well format plate is one of a 6, 12, 24, 48, 96, 384, or 1536 well plate.

15. The apparatus of claim 13, wherein at least one second member of the plurality of separate second members further comprises a distal extension that tapers outward to a third larger width from the second smaller width.

16. The apparatus of claim 15, wherein the third larger width is less than the first width.

17. The apparatus of claim 13, wherein the open distal end of each second member of the plurality of separate second members is configured to accommodate a probe of a forced air dryer apparatus while allowing gases to escape from the sample well around the probe without buildup of pressure inside the sample well.

18. The apparatus of claim 17, wherein the open distal end is configured to accommodate top down entry of the probe of the forced air dryer apparatus.

19. The apparatus of claim 17, wherein the open distal end is configured to accommodate side entry of the probe of the forced air dryer apparatus.

20. The apparatus of claim 13, wherein each first member of the plurality of separate open ended first members includes a chamfered outer edge configured to facilitate insertion of the first member into a sample tube.

21. The apparatus of claim 13, wherein the second member is at least one of funnel shaped, cone shaped, a pyramidal shape having at least three sides, or hourglass shaped.

22. The apparatus of claim 13, wherein the apparatus is fabricated from one or more of metal, polypropylene, polyethylene, polycarbonate, silicone, silicone rubber, thermoplastic polymers, or neoprene rubber.

23. A method for preventing cross-contamination of samples prepared in close proximity to one another, the method comprising:
providing at least two sample tubes, wherein each sample tube of the at least two sample tubes includes a sample to be analyzed;
fitting a separate sample tube adapter, of a plurality of sample tube adapters, into each sample tube of the at least two sample tubes, each separate sample tube adapter configured to prevent cross-contamination between separate sample tubes of the at least two sample tubes, each separate sample tube adapter including
an open proximal end defined by a first member configured to be inserted into one sample tube of the at least two sample tubes;
a tapered member that that tapers distally from a first width adjacent to the first member to a second smaller width at a distal end of the separate sample tube adapter; and
an open distal end providing a narrowed exit site defined by the tapered member, wherein the open distal end is configured to allow gases to escape from the one sample tube with increased velocity without buildup of pressure inside the one sample tube; and
with the plurality of sample tube adapters in place, performing at least one sample preparation step to prepare the samples to be analyzed for analysis.

24. The method of claim 23, wherein the at least one sample preparation step includes a forced air drydown step to remove a volatile solvent from each sample of the samples to be analyzed.

25. The method of claim 24, wherein the forced air drydown step includes, for each sample tube adapter fitted to a separate sample tube of the at least two sample tubes:
inserting a probe of a forced air drydown apparatus through the open distal end of the sample tube adapters;
passing a stream of a gas through the probe over the sample in the separate sample tube; and
expelling a stream of evaporated solvent from the sample and the gas delivered by the probe out of the separate sample tube through the open distal end of the sample tube adapter.

26. A kit, comprising:
a multi-well format plate; and
a mat having a bottom surface and a top surface, the bottom surface of the mat configured to fit onto the multi-well format plate, the bottom surface of the mat including a plurality of separate open ended first members configured to fit into a corresponding plurality of sample tubes of the multi-well format plate, the top surface of the mat including a plurality of separate second members in fluid communication with each first member of the first members, each tapered member including
- a tapered portion that that tapers distally from a first width adjacent to a separate first member of the plurality of separate open ended first members to a second smaller width at a distal end of a separate second member of the plurality of separate second members; and
- an open distal end providing a narrowed exit site defined by the tapered portion, wherein the open distal end is configured to allow gases to escape from a sample tube of the plurality of sample tubes with increased velocity without buildup of pressure inside the sample tube.

27. The kit of claim 26, wherein the multi-well format plate is one of a 6, 12, 24, 48, 96, 384, or 1536 well plate.

* * * * *